US006974833B2

(12) United States Patent
Rath

(10) Patent No.: US 6,974,833 B2
(45) Date of Patent: Dec. 13, 2005

(54) SYNERGISTIC COMPOSITIONS COMPRISING ASCOBATE AND LYSINE FOR STATES RELATED TO EXTRA CELLULAR MATRIX DEGENERATION

(76) Inventor: Matthias Rath, 20350 Stevens Creek Blvd., Apt. 405, Cupertino, CA (US) 95014

( * ) Notice: Subject to any disclaimer, the term of this patent is extended or adjusted under 35 U.S.C. 154(b) by 0 days.

(21) Appl. No.: 09/761,395

(22) Filed: Jan. 16, 2001

(65) Prior Publication Data

US 2002/0128309 A1 Sep. 12, 2002

(51) Int. Cl.$^7$ ................... A61K 31/34; A61K 31/355; A61K 31/198
(52) U.S. Cl. ............... 514/474; 514/274; 514/428; 514/458; 514/561; 514/562; 514/564; 514/567; 514/568; 514/763
(58) Field of Search ................. 514/274, 474, 514/561, 564, 567, 458, 428, 568, 562, 763

(56) References Cited

U.S. PATENT DOCUMENTS

| | | | |
|---|---|---|---|
| 5,198,465 A | 3/1993 | Dioguardi | |
| 5,278,189 A | 1/1994 | Rath et al. | |
| 5,626,883 A | 5/1997 | Paul | |
| 5,639,787 A | 6/1997 | Riordan et al. | |
| 5,650,418 A | 7/1997 | Rath et al. | |
| 5,891,459 A | 4/1999 | Cooke et al. | |
| 5,962,517 A | * 10/1999 | Murad | .......... 514/474 |

FOREIGN PATENT DOCUMENTS

| | | |
|---|---|---|
| DE | 34 40 090 A1 | 11/1984 |
| DE | 4243363 | 6/1994 |
| EP | 0 891 771 | 7/1997 |
| EP | 1 068 868 A2 | 7/1997 |
| EP | 891 771 A1 * | 1/1999 |
| FR | 2 753 098 | 9/1996 |
| GB | 2 029 220 | 3/1980 |
| GB | 2 268 871 | 1/1994 |
| JP | 62048622 | 3/1987 |
| JP | 4243825 | 8/1992 |
| JP | 6256184 | 9/1994 |
| WO | 91/19488 | 12/1991 |
| WO | 94/01006 | 1/1994 |
| WO | 95/28084 | 10/1995 |
| WO | 00/07607 | 2/2000 |
| WO | 01/22958 A2 | 4/2001 |

OTHER PUBLICATIONS

CA132:156872, Kosab, WO 2000007607 A1, 2/1000, abstract.*
Strickland, S., et al., (1976) J. Biol. Chem. 751:5694–5702.
Unkeless, et al. (1974) J. Biol. Chem. 249:4295–4305.
Skriver, et al. (1984) J. Cell Biol. 99:753–758.
Corasanti, et al. (1980) J. Natl. Canc. Inst. 65:345–351.
Ladehoff, A. (1962) Act, Path. Micro. Scand. 55:273–280.
Brown, M., et al., (1987) Nature 330: 113–114.
McLean, J.W., et al.(1987) Nature 300:132–137.
Eaton, D.L., (1987) Proc. Natl. Acad. Sol. USA 84:3224–3228.
Salonen, E.,et al. (1989) EMBO J. 8:4035–4040.
Harpel, P.C. et al.(1989) Proc. Natl. Acad. Sci. USA 86:3847–3851.
Gonzalez–Gronow, M. et al.(1989) Biochemistry 28:2374–2377.
Miles, L. et al.(1989) Nature 339:301–302.
Hajjar, K.A., et al.(1989) Nature 339:303–305.
Knox, E.A. (1973) Lancet, i.e. 1465–1467.
Wright, L.C. et al. (1989) Int. J. Cancer 43:241–244.
Rath, M. & L. Pauling (1990) Proc. Natl. Acad. Sci. USA 87:6204–6207.
Marcus, G. (1984) Sem. Thromb. Hemost. 10:61–70.
Nathan, C. (1987) J. Clin. Invest. 79:319–326.
Murad, et al. 1981 Proc. Natl. Acad. Sci. USA 78:2879–2882.
Yonemoto, et al.1976 Proc. Amer. Assoc. Canc. Res. 17:288.
Aoki, N. et al. (1978) Blood 52:1–12.
Katz, E.A., "Reduction of Cholesterol and Lp(a) and Regression of Coronary Artery Disease: A Case Study" *Journal of Orthomolecular Medicine* pp. 173–179, 11/3, 1996.
Conner, W.E., "What Role for Dietary Supplements in Preventing Coronary Heart Disease?" *Consultant* p. 1413 38/6 1998.
Mukhopadhyay, C.K., et al "Free Metal Ion–independent Oxidative Damage of Collagen" *The Journal of Biological Chemistry* pp. 30200–30205, vol. 269, No. 48, 1994.
Tinker, D. et al. "Role of Selected Nutrients in Synthesis, Accumulation, and Chemical Modification of Connective Tissue Proteins" *Physiological Reviews* pp. 607–657, vol. 65, No. 3, 1985.
Murad, S. et al. "Collagen Synthesis in Cultured Human Skin Fibroblasts: Effect of Ascorbic Acid and Its Analogs" *The Journal of Investigative Dermatology* pp. 158–162, vol. 81 No. 2, 1983.
Bostom, A.G., et al. "The Effect of High–Dose Ascorbate Supplementation on Plasma Lipoprotein(a) Levels in Patients With Premature Coronary Heart Disease" *Pharmaco Therapy* pp. 458–464, vol. 15, No. 4, 1995.

(Continued)

Primary Examiner—Phyllis G. Spivack
(74) Attorney, Agent, or Firm—Kenyon & Kenyon

(57) ABSTRACT

Methods for the treatment of diseases or pathological states related to the degradation of the extracellular matrix, such as degenerative diseases atheriosclerosis, cancer, infection or other inflammatory diseases are disclosed, comprising administering compositions of lysine, proline, ascorbate, and their derivatives and synthetic analogues and vitamins, pro-vitamins and trace elements.

2 Claims, 4 Drawing Sheets

OTHER PUBLICATIONS

Tardif, J–C et al. "Probucol and Multivitamins in the Prevention of Restenosiss After Coronary Angioplasty" *The New England Journal of Medicine* pp. 365–372, vol. 337, No. 6, 1997.

Rath, Matthias, M.D. et al. "Nutritional Supplement Program Halts Progression of Early Coronary Atherosclerosis, Documented by Ultrafast Computed Tomography" *The Journal of Applied Nutrition*, vol. 48, No. 3, 1996.

* cited by examiner

SYNERGISTIC COMPOSITIONS COMPRISING ASCOBATE AND LYSINE FOR STATES RELATED TO EXTRA CELLULAR MATRIX DEGENERATION

FIELD OF INVENTION

The present invention relates to substances and compositions for the prevention and treatment of diseases or pathological states related to the degradation of the extracellular matrix, such as including but not limited to degenerative diseases, particularly arteriosclerosis, cancer, infections or other inflammatory diseases.

BACKGROUND OF THE INVENTION

From studies of ovulation in mammals, it appears that gondadotropins, prostaglandins and certain other substances stimulate the release of plasminogen activator (PA) from follicle cells embedded in the ovarian stroma (Strickland, S., et al., (1976) J. Biol. Chem. 751:5694–5702) (FIG. 1). PA then stimulates the extracellular activation of plasminogen to plasmin. Plasmin is known to activate procollagenase to collagenase, which then degrades collagen.

Under pathological conditions, PA is also secreted by cancer cells, macrophages and virally transformed cells in a manner similar to follicle cells that have been hormonally stimulated (Unkeless, et al. (1974) J. Biol. Chem. 249:4295–4305) (FIG. 2). PA has been found in high concentrations in metastasizing lung tumors (Skriver, et al. (1984) J. Cell Biol. 99:753–758). PA has also been found in association with a variety of human tumors, as well as kidney and bladder carcinomas (Corasanti, et al. (1980) J. Natl. Canc. Inst. 65:345–351 Ladehoff, A. (1962) Act, Path. Micro. Scand. 55:273–280).

A particular role in the regulation of this mechanism has been proposed for lipoprotein(a) (Lp(a)), a low-density-lipoprotein-like particle that carries a unique glycoprotein, called apoprotein (a) (apo(a)). It has been proposed that this particle participates in wound healing and general cell repair (Brown, M., et. al., (1987) Nature 330:113–114). The cDNA sequence of apo(a) shows a striking homology to plasminogen, with multiple repeats of kringle 4, one kringle 5, and a protease domain. The isoforms of apo(a) vary in the range of 300 to 800 kDa and differ mainly in their genetically determined number of kringle 4 structures (McLean, J. W., et al.(1987) Nature 300:132–137). While apo(a) has no plasmin-like protease activity (Eaton, D. L., (1987) Proc. Natl. Acad. Sol. USA 84:3224–3228), serine protease activity has been demonstrated (Salonen, E.,et al. (1989) EMBO J. 8:4035–4040).

Despite its lack of functional homology, the strong structural similarity to plasminogen is decisive in the understanding of the physiological and pathological role of Lp(a). Like plasminogen, Lp(a) has been shown to bind lysine-sepharose, immobilized fibrin and fibrinogen, and the plasminogen receptor on endothelial cells (Harpel, P. C. et al.(1989) Proc. Natl. Acad. Sci. USA 86:3847–3851; Gonzalez-Gronow, M. et al.(1989) Biochemistry 28:2374–2377 Miles, L. et al.(1989) Nature 339:301–302 Hajjar, K. A., et al.(1989) Nature 339:303–305). Furthermore, Lp(a) has been shown to bind to other components of the arterial wall such as fibronectin and glycosaminoglycans. The precise nature of these bindings, however, is poorly understood.

Lp(a) plasma levels are found to be elevated in cancer, atherosclerosis and other diseases. Inversely, low levels of ascorbate have been associated with high incidences of these diseases (Knox, E. A. (1973) Lancet, i.e. 1465–1467; Wright, L. C. et al. (1989) Int. J. Cancer 43:241–244). Based on this and other observations, it was suggested that Lp(a) is a surrogate for ascorbate (Rath, M. & L. Pauling (1990) Proc. Natl. Acad. Sci. USA 87:6204–6207).

There exists a need for a therapeutic composition to reduce the degradation of the extracellular matrix, particularly due to plasmin-induced and free radical-induced proteolysis respectively fibrinolysis. Of particular value would be a composition that simultaneously reduces degradation and enhances collagen synthesis, the primary component of the extracellular matrix, and thereby help to prevent the proliferation of diseases.

SUMMARY OF THE INVENTION

A pharmaceutical composition is provided for the treatment of degenerative diseases having their origins in the destruction of the extracellular matrix comprising administering a therapeutic composition comprising at least one fibrinolysis inhibitor in an amount sufficient to decrease plasmin—and free radical—mediated production of collagenase to a subject in need of such treatment.

Another aspect of the invention is a composition which comprises an activator suitable for the enhancement of collagen synthesis.

Another aspect of the invention provides a composition comprising ascorbate, and optionally one or more antioxidants. The term antioxidant throughout the specification and the claims is intended to exclude ascorbate, which itself is a powerful antioxidant.

Also provided as an aspect of the present invention is a therapeutic composition comprising at least one fibrinolysis inhibitor, one collagen synthesis activator, ascorbate, and optionally one or more antioxidants, in amounts sufficient to decrease plasmin—and free radical—mediated production of collagenase.

These and other aspects of the invention will be more readily understood upon consideration of the following drawings and the detailed description of embodiments of the invention.

DETAILED DESCRIPTION OF THE INVENTION

The present invention relates to methods and compositions that slow or inhibit extracellular matrix degradation, thereby proving useful for the treatment of cancer, degenerative diseases, infections or other inflammatory diseases or pathological states related to the degradation of the extracellular matrix. A number of diseases appear to arise or become exacerbated as a result of degradation of the extracellular matrix. Cancer, for instance, becomes most life threatening after an individual tumor has metastasized, that is, after individual cells have broken free of the extracellular matrix and been carried away to other parts of the body where they can proliferate. Beside cancer, other degenerative diseases like advanced atherosclerosis have similar mechanisms by which the disease proliferates.

Figure 1:
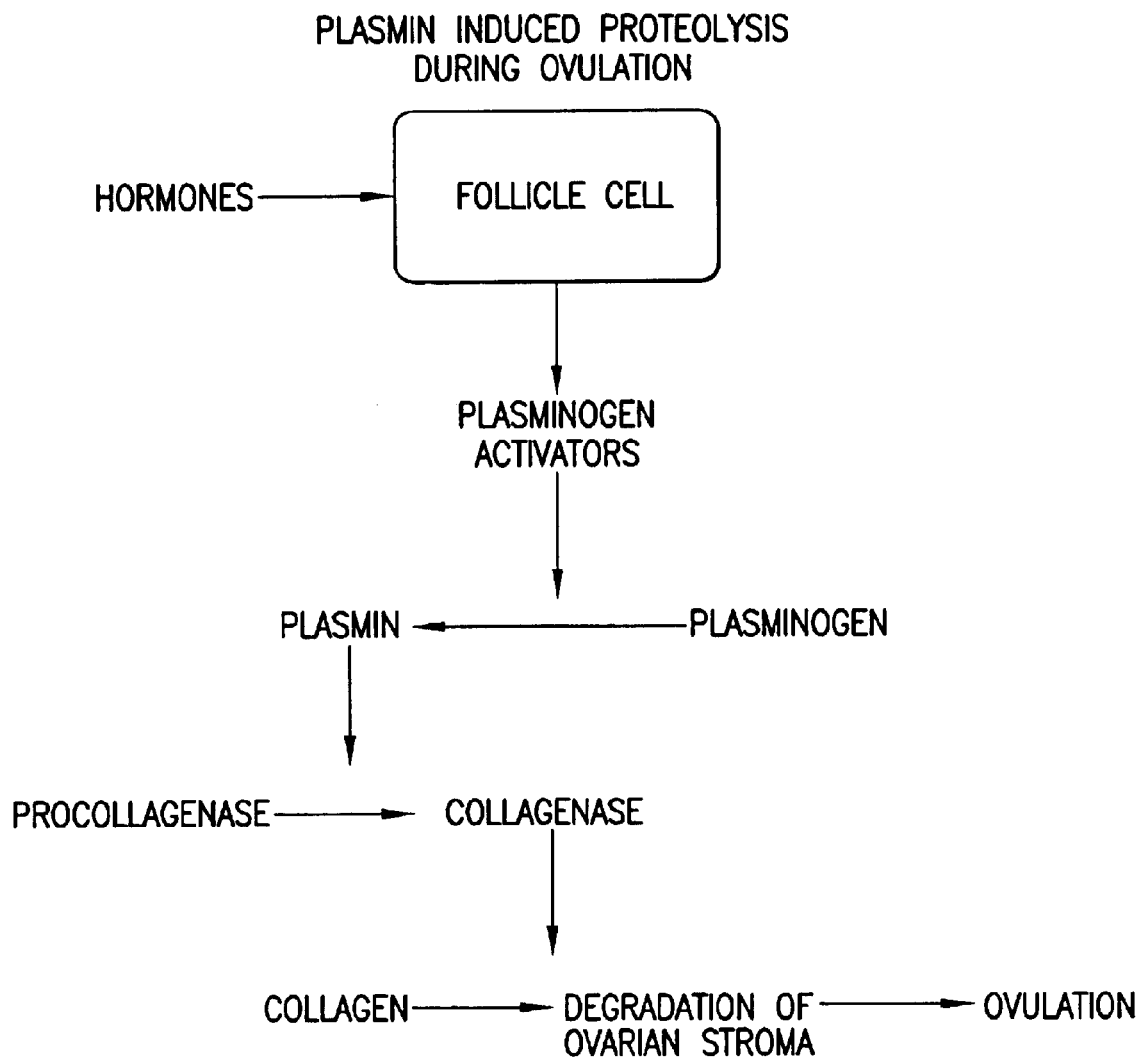
FIG. 1 is a flow chart of plasmin-induced tissue degradation under physiological conditions leading to ovulation.
Figure 2:
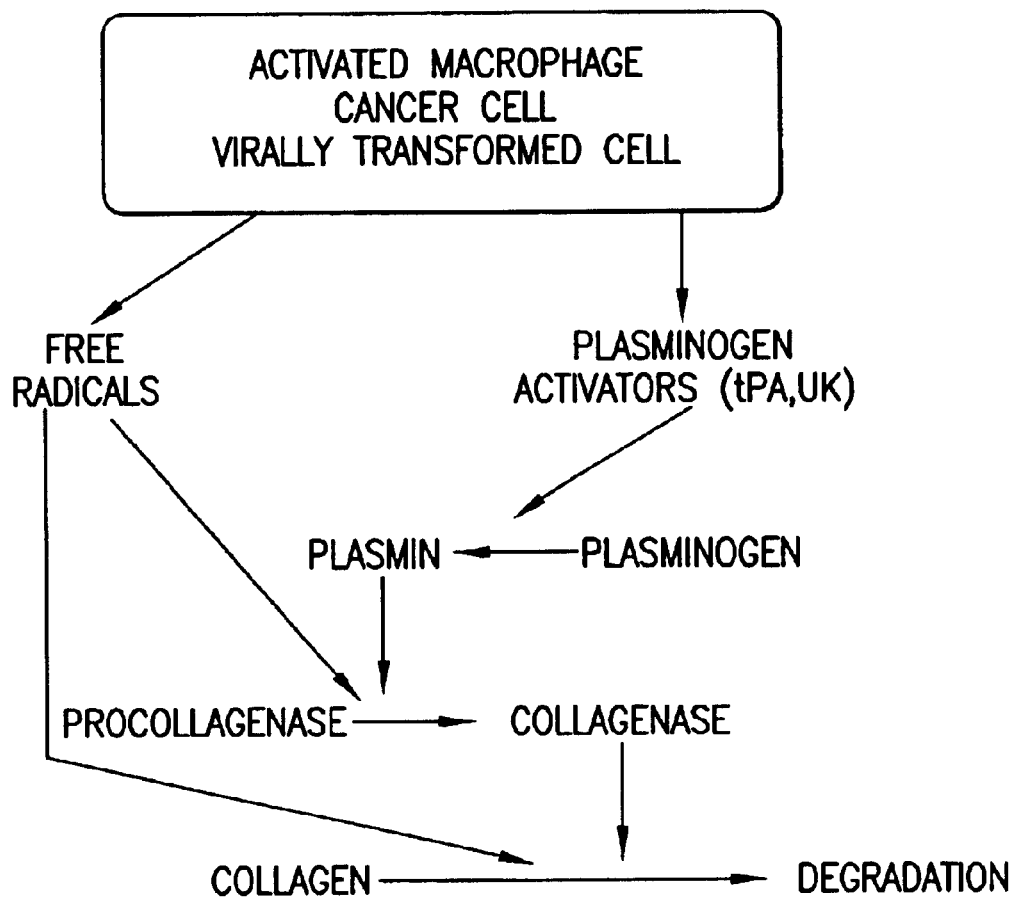
FIG. 2 is a flow chart of the physiology of the genesis of degeneration of the extracellular matrix as a result of free radical induced proteolysis.

As used herein, the term "collagenase-linked degenerative diseases" includes degenerative diseases, neoplastic diseases, infections or other inflammatory diseases or pathological states related to the degradation of the extracellular matrix. As shown in FIG. 2, two basic pathomechanisms are plasmin-induced and free radical-induced proteolysis, which may well act synergistically in fulminant disease progression. Particularly in the case of cancer, treatment has focused on removing or killing tumors and little attention has been paid to inhibiting proliferation or finding methods of tumor containment, other than surgery. This containment can be achieved by substances interfering with or blocking these pathomechanisms, such as fibrinolysis inhibitors. In a few instances, tranexamic acid has been administered in an attempt to stop cancer proliferation, with inconclusive results (Marcus, G. (1984) Sem. Thromb. Hemost. 10:61–70).

The present invention is based in part on the discovery that plasmin-induced proteolysis is a fundamental physiological feature in humans responsible for the regulation of many different, seemingly unrelated physiological processes. In particular, cancer cells and normal tissues alike within the body secrete PA which activates plasmin and thereby results in collagen degradation where a degeneration of the extracellular matrix is beneficial to the secreting tissue. For example, the stroma of the follicle of the human ovary must degenerate in order to release the ovum into the reproductive tract. Follicle cells secrete PA which activates plasminogen to form plasmin. Plasmin promotes the collagenase which then proteolyses the extracellular matrix of the stroma allowing the follicle to expand, rupture and discharge the ovum. Many cancer cells also produce large amounts of PA which then operates within the same physiological pathway eventually leading to the degeneration of collagen and the extracellular matrix. Except in this instance, degeneration has the deleterious effect of allowing individual cells within a tumor to free themselves so that they may be carried to distant parts of the body. It appears that metastasis in all cancers depends to a great extent upon degradation of the extracellular matrix.

As set forth in greater detail in U.S. patent application Ser. No. 07/533,129, it has also been discovered that certain substances compete with plasminogen and Lp(a) for binding sites on the endothelial cells of blood vessel walls. It has now been discovered that these substances, previously called Lp(a) binding inhibitors and herein called fibrinolysis inhibitors, are antagonistic to plasmin in its conversion of procollagenase to collagenase. Thus, it is disclosed that the administration of these fibrinolysis inhibitors, especially in combination with ascorbate which promotes collagen synthesis, can prevent or at least retard the degradation of the extracellular matrix due to an increased activation of plasmin.

The term fibrinolysis inhibitor throughout the specification and claims is intended to include all substances that act as an antagonist for plasmin-induced proteolytic activity, particularly fibrinolysis induced production of collagenase. Some of these compounds, in high doses, are in clinical use for the treatment of hyperfibrinolytic states.

In the initiation and propagation of most pathological conditions, activated macrophages play an important role. When activated, these cells secrete a variety of products including enzymes such as procollagenases. Moreover, as shown in FIG. 2, they secrete reactive oxygen intermediates such as superoxide, hydrogen peroxide, and hydroxyl radical, hereinafter called "free radicals." Nathan, C. (1987) J. Clin. Invest. 79:319–326. Thus, another mechanism of disease proliferation is mediated by peroxyl free radicals. These oxidative radicals can be generated by activated macrophages and other cells, particularly under pathological conditions. Similar to plasmin-induced proteolysis, free radicals induce the degradation of the extracellular matrix and thereby promote disease progression. Free radicals are known to induce proteolysis in several ways, an important one being the activation of procollagenase to collagenase. Ascorbate is a powerful antioxidant and is thus an important therapeutic agent for limiting free radical proteolysis.

Figure 4:
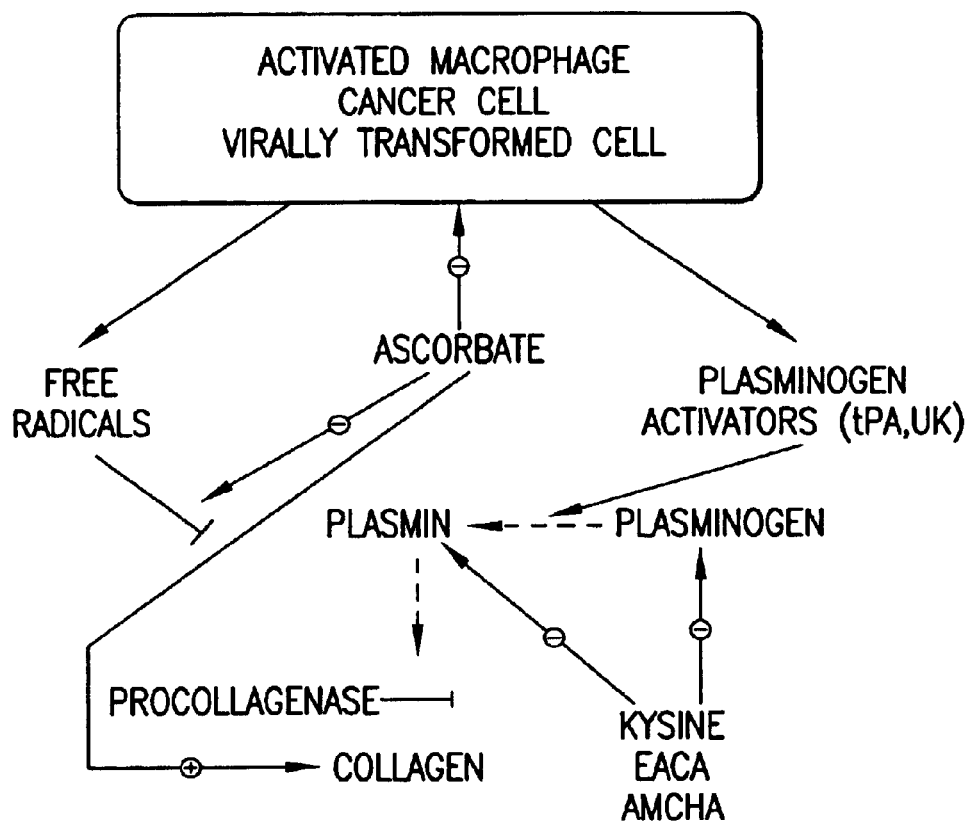
FIG. 4 is a flow chart of the synergistic effect of ascorbate and fibrinolysis inhibitors in the therapy of plasmin and free radical-induced proteolysis.

As shown in FIG. 4, the beneficial effects of ascorbate suggest that ascorbate in combination with these fibrinolysis inhibitors has a synergistic effect and inhibits plasmin induced as well as free radical-induced proteolysis. Ascorbate promotes the production of collagen (Murad, et al.1981 Proc. Natl. Acad. Sci. USA 78:2879–2882), and also stimulates production of lymphocytes which may be of use in combating cancer cells already formed (Yonemoto, et al. 1976 Proc. Amer. Assoc. Canc. Res. 17:288).

Fibrinolysis inhibitors inhibit the dissolution of blood clots, thus having a pro-coagulative effect. These properties so far have limited or prevented the use of these agents in the treatment of cancer and other diseases, since it is known that neoplasms are frequently associated with thromboembolic complications. Ascorbate is known to have anti-coagulative properties by stimulating for example prostracyclin and inhibiting thromboxane formation. Thus the aspect of the invention wherein fibrinolysis inhibitors are combined with ascorbate would greatly increase the use of this therapy by eliminating undesired side-effects of a mono-therapy. The present invention provides methods and compositions for both the treatment and prevention of diseases associated with the degradation of extracellular matrix. Each of these embodiments is discussed in nim below.

General Application

The present invention provides a method and composition for the treatment and prevention of collagen-linked degenerative diseases like cancer and many others by administering to a subject an effective amount of at least one fibrinolysis inhibitor which inhibit plasmin- and free radical-mediated conversion of procollagenase to collagenase. In this way, destruction of the extracellular matrix, which is predominantly formed of collagen, is reduced or eliminated.

Preferred fibrinolysis inhibitors include, but are not limited to α-aminocaproic acid (EACA), lysine, tranexamic acid (4-aminomethylcyclohexane carboxylic acid), p-aminomethylbenzoic acid (PAMBA), p-benzylamine sulfuric acid, α-N-acetyl-lysine-methyl ester, cis/trans-4-aminomethylcyclohexane carboxylic acid-(1) (AMCHA), trans-4-aminomethylcyclohexane carboxylic acid (AMCA), and 4-aminomethyl-bicyclo-2,2,2-octane carboxylic acid (AMBOCA). An effective amount of a fibrinolysis inhibitor or a mixture of one or more fibrinolysis inhibitors may also be used. Thus, by combination of two or more fibrinolysis inhibitors, one could potentially increase the therapeutic effect, while decreasing the toxicity because the fibrinolytic substances may have different catabolic pathways.

In addition, the present method and composition can include ascorbate in combination with the fibrinolysis inhibitors. As used herein, the term "ascorbate" includes any pharmaceutically acceptable salt of ascorbate, including sodium ascorbate, as well as ascorbic acid itself.

Other substances used in the treatment of cardiovascular disease may also be co-administered, including antioxidants, such as tocopherol, carotene, selenium, N-acetylcysteine, probucol and related substances, vitamins, provitamins, and trace elements.

Although ascorbate can be used alone because of its stimulating effects on collagen synthesis, it is preferred when treating a pre-existing degenerative disease to combine ascorbate with at least one each of the fibrinolysis inhibitors and antioxidants in the dosages (per kilogram of body weight per day (/kg BW/d) provided in Table 1. It should be noted that Table 1 provides differing concentration ranges of each constituent, depending upon whether the composition is to be administered orally or parenterally. The variance in dosages is reflective of variation in disease severity. It will be realized therefore that if the subject has been diagnosed for advanced stages of a particular degenerative disease, dosages at the higher end of this range could be utilized. However, if prevention of collagen degradation is desired prior to onset of severe symptoms, dosages at the lower end of this range may be utilized.

As an alternative, a pharmaceutical composition identical to the one just described, but omitting ascorbate, may be employed. Where ascorbate and fibrinolysis inhibitors are utilized in the same composition, they may simply be mixed or may be chemically combined using synthesis methods well known in the art, such as compounds in which ascorbate and the inhibitor are covalently linked, or form ionically-bound salts. For example, ascorbate may be bound covalently to lysine, other amino acids, or $\epsilon$-aminocaproic acid by ester linkages. Ascorbyl $\epsilon$-aminocaproate or ascorbyl-aminomethylcyclohexane carboxylic acid are such examples. In this form the ascorbate moiety may be particularly effective in also preventing undesirable lipid peroxidation.

Ascorbate and fibrinolysis inhibitors alone or in any combination may be used together with other agents used in the chemotherapeutic treatment of cancer. These agents include, but are not limited to, compounds from the groups of antibiotic derivatives, anti-estrogens, antimetabolics, hormones, cytotoxic agents, nitrogen-mustard derivatives or steroids and combinations of these. In the case of oral administration, a pharmaceutically acceptable and otherwise inert carrier may be employed. Thus, when administered orally, the active ingredients may be administered in tablet form. The tablet may contain a binder such as tragacanth, corn starch or gelatin; a disintegrating agent, such as alginic acid, and/or a lubricant such as magnesium stearate. If administration in liquid form is desired, use of sweetening and/or flavoring agents may be used. If administration is by parenteral injection, in isotonic saline, a phosphate buffered solution or the like, may be used as pharmaceutically acceptable carrier.

In addition, the amino acid proline, proline salts or synthetic proline analogs may be used in the prevention and treatment of the pathological conditions described in this patent.

Beside its role as an inhibitor of Lp(a)-binding proline, it is also required as an amino acid component for protein synthesis. Collagen and other extracellular matrix proteins are particularly rich in lysine and proline residues, which make up about 25% of the total mass of collagen.

While proline—as opposed to lysine—can be synthesized in the body, the synthesis rate of this amino acid is suboptimal especially in chronic diseases. In these pathological states, where there is an excess of collagen degradation lasting over months or even years the synthesis of collagen and other extracellular matrix molecules, sufficient availability of proline becomes a critical factor, determining optimum production of new collagen and, thereby, containing the progression of diseases.

Therefore, it is essential that an adequate amount of proline, proline salts and proline analogs is available in the body.

The advisability of using fibrinolysis inhibitors in treating cancer, angiohematoma and other such diseases will depend to some extent on the subject's general health, particularly with regard to hyperfibrinolytic conditions. Most fibrinolysis inhibitors (except lysine) are used clinically to treat such conditions. As a result, monitoring of the subject's coagulation and fibrinolytic system is recommended before and during treatment. It should however be noted that hemostatic complications are unlikely, since these fibrinolysis inhibitors are general protease inhibitors which have also been shown to inhibit coagulation. Aoki, N. et al. (1978) Blood 52:1–12. Long-term administration of fibrinolysis inhibitors will require formulations in which the dosages of fibrinolysis inhibitors are in the lower ranges of the dosages given in Table 2. As mentioned above, ascorbate is known to stimulate prostaglandin and prostacyclin synthesis and decrease thromboxane levels, thus exerting an anti-aggregatory effect. These properties may be particularly desireable in combination with the use of fibrinolytic inhibitors to counteract potential coagulative side-effects.

The ascorbate and the fibrinolysis inhibitors described above may be separately administered. Further optimization of therapeutic effect can be gained by using a time release composition to achieve relatively constant serum concentrations of the agent through time.

TABLE 1

Dosages of Components in the Compositions of the Present Invention

| | Oral Administration | Parenteral Administration |
|---|---|---|
| Ascorbate: | | |
| EACA | 5–500 mg/kg BW/d | 25–2500 mg/kg |
| Tranexamic Acid | 1–1500 mg/kg BW/d | same |
| Para-aminomethyl benzoic acid | 1–500 mg/kg BW/d | same |
| | 1–500 mg/kg BW/d | same |
| Lysine | 1–1500 mg/kg BW/d | same |
| Proline | 1–1500 mg/kg BW/d | same |
| Antioxidants: | | |
| Tocopherol | 0.1–500 1U/kg BW/d | same |
| Carotene | 0.1–10,000 1U/kg BW/d | same |
| N-acetyl cysteine | 0.1–5,000 mg/kg BW/d | same |

Figure 3:
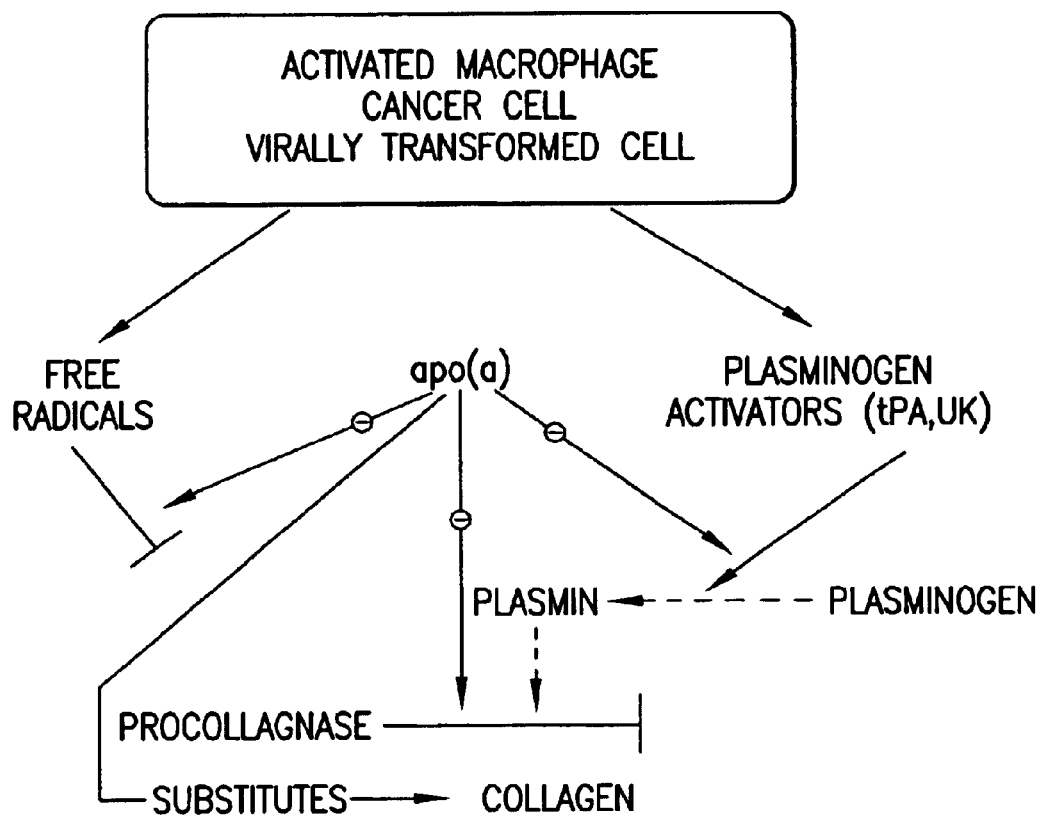
FIG. 3 is a flow chart showing the physiological role of apo(a) in the co-regulation of plasmin and free radical induced proteolysis.

Referring to FIG. 3, another aspect of the invention is the discovery that Lp(a) is a co-regulator of plasmin-induced proteolysis critically involved in tissue transformation and repair. Due to its homology to plasminogen and plasmin, it is a physiological competitive inhibitor of plasmin-induced proteolysis. Moreover, apoprotein(a) has over 100 disulfide bonds and therefore functions as an antioxidant like other protein-thiols.

All publications and patent applications cited in this specification are herein incorporated by reference as if each individual publication or patent application were specifically and individually indicated to be incorporated by reference. It is now apparent that the compositions and therapeutic methods of the present invention for prevention and treatment of pathological states related to degeneration of the extracellular matrix show marked improvements over known methods and it is to be understood that although certain preferred embodiments have been disclosed, illustrated and described above, other embodiments are possible without departing from that which is the invention described herein. It is intended therefore that the invention be defined by the claims that follow as well as the equivalents thereof.

What is claimed is:

1. A method for treatment of a collagenase-linked degenerative disease in a mammal in need thereof comprising administering to the mammal a therapeutic effective amount of a composition comprising:

i) at least one collagen synthesis activator selected from the group consisting of ascorbyl ε-aminocaproate, and ascorbyl aminomethylcyclohexane carboxylic acid;

ii) at least one fibrinolytic inhibitor selected from the group consisting of ε-aminocaproic acid, tranexamic acid, p-aminomethylbenzoic acid, p-benzylamine sulfuric acid, α-N-acetyl-lysine-methyl ester, cis/trans-4-aminomethylcyclohexane carboxylic acid, trans-4-aminomethycyclohexane carboxylic acid, 4-aminomethyl-bicyclo-2,2.2-octane carboxylic acid, natural lysine and proline;

iii) at least one anti-oxidant selected from the group consisting of tocopherol, carotene and N-acetyl cysteine, selenium, and probucol; and iv) a pharmaceutically acceptable carrier, wherein the i)–iv) ingredients of the composition function to inhibit extracellular matrix degradation and stimulate collagen synthesis so as to treat the collagenase-linked degenerative disease.

2. The method according to claim 1, wherein the composition is administered orally or parenterally.

* * * * *